(12) United States Patent
Wadman (10) Patent No.: US 7,978,332 B2
(45) Date of Patent: Jul. 12, 2011

(54) OPTICAL MEASUREMENT DEVICE

(75) Inventor: Sipke Wadman, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 444 days.

(21) Appl. No.: 12/296,974

(22) PCT Filed: Apr. 10, 2007

(86) PCT No.: PCT/IB2007/051265
§ 371 (c)(1),
(2), (4) Date: Oct. 13, 2008

(87) PCT Pub. No.: WO2007/119199
PCT Pub. Date: Oct. 25, 2007

(65) Prior Publication Data
US 2009/0279097 A1   Nov. 12, 2009

(30) Foreign Application Priority Data
Apr. 18, 2006   (EP) ..................................... 06112697

(51) Int. Cl.
*G01N 21/47* (2006.01)
(52) U.S. Cl. ........................................ 356/446; 356/445
(58) Field of Classification Search .......... 356/445–448, 356/369; 250/353, 336.1; 600/310
See application file for complete search history.

(56) References Cited

U.S. PATENT DOCUMENTS

| | | | |
|---|---|---|---|
| 4,661,706 A | 4/1987 | Messerschmidt et al. | |
| 6,577,393 B1 | 6/2003 | Potzschke et al. | |
| 2001/0021802 A1 | 9/2001 | Messerschmidt et al. | |
| 2005/0018203 A1 | 1/2005 | Hogan | |
| 2006/0092418 A1 | 5/2006 | Xu et al. | |

FOREIGN PATENT DOCUMENTS

| | | |
|---|---|---|
| EP | 0612996 A2 | 8/1994 |
| GB | 2304187 A | 3/1997 |

(Continued)

OTHER PUBLICATIONS

P. Matousek, et al: Subsurface Probing in Diffusely Scattering Media Using Spatially Offset Raman Spectroscopy, Applied Spectroscopy, The Society for Applied Spectroscopy, vol. 59, No. 4, Apr. 2005, pp. 393-400.

*Primary Examiner* — Gregory J Toatley
*Assistant Examiner* — Tri T Ton
(74) *Attorney, Agent, or Firm* — Sherry Womack (57) ABSTRACT

An optical measurement device for measuring the optical appearance of a surface (12) of a sample (10), in particular a surface (12) of a human skin, wherein the surface is at least partly translucent, comprising: an illumination device (18) for illuminating the surface (12) with an illumination beam (20), wherein the illumination beam (20) is generated from a radiation beam emitted from a radiation source (58), a detection device (56) for intercepting a response beam (30, 32), wherein the response beam (30, 32) is generated as a response of the sample (10) to the illumination beam (20), incident on the surface (12). The optical measuring device comprises a measuring head (14), that can be brought into contact with the surface (12) of the sample (10), wherein the measuring head (14) comprises at least one elongated aperture (40) that is designed such that the response beam (30, 32), generated below the surface (12) in a sub-surface area (16) of the sample (10), is detected by the detection device (56), wherein the illumination beam (20) directly reflected at the surface is cut off.

21 Claims, 5 Drawing Sheets

FOREIGN PATENT DOCUMENTS

| | | | |
|---|---|---|---|
| WO | 9639922 | A1 | 12/1996 |
| WO | 9719341 | A1 | 5/1997 |
| WO | 0037923 | A1 | 6/2000 |
| WO | 03067229 | A1 | 8/2003 |
| WO | 2004027402 | A1 | 4/2004 |
| WO | 2004038388 | A1 | 5/2004 |
| WO | 2004077032 | A1 | 9/2004 |
| WO | 2004077033 | A1 | 9/2004 |
| WO | 2005015179 | A1 | 2/2005 |
| WO | 2005063116 | A1 | 7/2005 |
| WO | 2005079662 | A1 | 9/2005 |

OPTICAL MEASUREMENT DEVICE

The invention relates to an optical measurement device for measuring an optical appearance of a surface of a sample, in particular the surface of a human skin, wherein the surface is at least partly translucent, comprising an illumination device for illuminating the surface with an illumination beam, wherein the illumination beam is generated from a radiation beam emitted from a radiation source, and a detection device for intercepting a response beam, wherein the response beam is generated as a response of the sample to the illumination beam incident on the surface.

The invention relates further to a method for measuring an optical appearance of a translucent surface of a sample, in particular a human skin, comprising the steps of illuminating the surface and detecting a response beam, wherein the response beam is generated as a response of the sample to the illumination beam incident on the surface.

Such an optical measurement device for measuring an optical appearance is known from the GB 2 304 187 A.

The optical appearance of a surface a the sample is the result of what the surface does with light from the environment, in particular is the optical appearance determined by a sum of an overall response of the surface to the light, called illumination beam in the following, incident on the surface.

The optical appearance can be shiny and glossy or dull, rough or smooth, with a texture of a preferred direction or randomly textured. The surface may have a consistent color or color flops, the surface may be opaque or translucent or reflective like a mirror.

A radiation beam incident on the surface of the sample is—due to the macroscopic and microscopic properties of the surface, like roughness and texture and other material properties—reflected, scattered, absorbed, or changed in color. The direction of the texture, for instance, is visible due to the scattering of the illumination beam. As an example, a flat, shiny surface reflects a higher percentage of the incident radiation beam in the primary reflection direction as a dull surface.

Depending on the material of the sample and the property of the surface as well as the size and nature of the sample having the surface, different methods for an accessing of the optical appearance are known. In general, visual measurements are made by visually comparing the surface of the sample to a certain standard surface by trained personnel. A visual measurement device, like a gloss-meter or a color-meter for the measurement of the gloss or color, as well as a mechanical microgeometrical measurement device like a profilometer for the determination of the roughness of the surface are known.

An optical measurement device for measuring the optical appearance of a surface of the human skin is generally known. Such an optical measurement device comprises in general an illumination device and a detection device, intercepting the radiation transmitted, reflected and/or scattered from the sample.

A scatterometer is known from the U.S. Pat. No. 6,577,393. Herein, a radiation beam is directed onto a surface of a sample and a scattered and/or reflected light is intercepted by a screen having a special coating. The image of the screen imaged by a photo-sensitive device, in particular a camera.

Herein, the image in the camera is the Fourier-like transform of the scattered distribution of the reflected and/or scattered radiation beam.

Objects, which are opaque, have a surface which scatters the illumination beam at the surface, thereof. A translucent objects scatters the illumination beam at the surface and additionally below the surface in a sub-surface area.

The optical appearance of translucent objects is influenced by the surface properties mentioned above as well as by the degree of the translucency. Therefore, the overall determination of the optical appearance requires that the surface and the sub-surface areas are accessible by a measurement of the optical appearance.

An optical measurement device for a characterization of a translucent sample, in particular a tissue, is known from the GB 2 304 187 A, wherein a translucency of a material is established. The optical measurement device comprises a device for illuminating an area of the material and a device for detecting the intensity of the radiation leaving the material as a function of a distance from a illumination source. The device can be used in both, transmission mode and backscattering mode. Scattered light is collected by rod lenses and fed to a detector which is divided into a number of concentric rings. The resulting signal profile of intensity against distance from the illuminated area is analyzed by a neural network. The resulting measurements are used to determine a so-called translucency gradient.

The translucency gradient is only a feature of the sample summing up the overall effects influencing the optical appearance. On the other hand the above mentioned device for estimating the optical appearance is not able to differentiate between the different features like scattering centers causing the translucency.

Of particular interest is the investigation of the optical appearance of a human skin. The human skin is translucent material, wherein the translucent human skin both diffuse the illuminating beam and allows a significant amount of the illumination beam to pass through the material in all directions.

The optical appearance of the human skin is determined by the properties of the surface as well as by the properties of the sub-surface layers, because the human skin is translucent. The skin is influenced by physiological factors like a blood perfusion and/or a skin's melanin content of that moment.

Therefore, it is an object of the present invention to provide an optical measurement device, which is able to estimate the optical appearance of a sample with a translucent surface, in particular of a human skin. It should be possible to apply the optical measurement device to the skin of a human being, inspecting small surface areas thereof.

The object is solved according to the invention by an optical measurement device according to the one mentioned at the outset, in that the optical measurement device comprises a measuring head comprising at least one elongated aperture, wherein the at least one elongated aperture is designed such that the response beam, generated below the surface in a sub-surface area of the sample, is detectable by the detection device, wherein the illumination beam directly reflected at the surface is cut off.

The optical measurement device according to the present invention allows the estimation of the optical appearance of the human skin, because it has access to the surface and the sub-surface layers.

The optical measurement device of the invention will be discussed in the following in the context of the human skin, but it is also possible to use the device for the inspection of other translucent objects like light bulbs, paints, translucent coatings, plastics and the like.

The measuring head is positioned onto or very close to but not touching the surface of the sample and is inspected during the measurement. The illumination device is illuminating the surface with an illumination beam. Because the surface comprises a translucent material, the illumination beam is penetrating into the surface and is scattered at the surface and at a sub-surface area of the sample. The illumination beam scattered at the sub-surface area is re-emitted from the surface at a location different to the one of the illumination beam scattered at the surface. Therefore, the translucent sample generates a scattering pattern with a spatial distribution in three dimensions.

Therefore, the response beam emitted from the surface distributed in two dimensions is indicative for the distribution of the illumination beam scattered in the sub-surface area. The direct reflected illumination beam is cut-off. This is advantageous, because the intensity of the direct reflected illumination beam is much higher than the intensity of the scattered illumination beam.

A typical depth accessable with the optical device of the present invention is 10 to 20 mm. This is due to the fact that the radiation beam having an intensity at the surface is loosing intensity due to scattering processes on its way into the depth of the skin. The intensity decays with an 1/e function in a homogeneous sample. The skin has a complex structure and the decay function may show deviations from the 1/e shape accordingly. Typical scatter centers at the surface and at the sub-surface layers are pigments, bones, cartilage, adipose tissue, connective tissue, collagen, blood and others.

The deep scattered radiation is partly re-emitted from the surface, but away from the area where the illumination beam had entered the surface of the human skin. This scattered beam can be detected by the detection device of the optical measurement device, because the aperture has an elongated shape in one or more directions and gives therefore access to the spatial distribution of the scattered illumination beam in the sub-surface area. This is because the response beam can propagate through the elongated aperture towards the detection device.

According to a first preferred embodiment of the invention, the measurement head comprises a casing with a base plate comprising the at least one elongated aperture, wherein the base plate is arrangeable at the surface of the sample in order to perform a measurement of the optical appearance.

The base plate allows a defined positioning of the measuring head onto the human skin. The base plate has typical dimensions of several ten millimeters in length and a width between 10 mm and 20 mm, resulting in a small measuring head having a longish shape. Herein the shape of the casing is following the shape of the elongated aperture. The casing comprises preferably a small height in order to avoid shadowing of the illumination beam, scattered in the sub-surface area.

In principle, it is possible to divide the at least one elongated aperture into several smaller elongated apertures in order to obtain a masking effect in order to mask certain distances from an illumination spot, where the illumination is incident at the surface.

According to a further preferred embodiment of the invention, the illumination device comprises a fiber, wherein the radiation beam is directed by means of the fiber as the illumination beam onto the surface of the skin.

A fiber is a flexible optical component having a small exit window for the illumination beam to escape. Therefore, a small radiation beam, called illumination spot, can be directed onto the surface. A good spatial resolution of the estimated optical appearance can be achieved using a small illumination spot.

Using the fiber to direct the illumination beam onto the surface of the sample to be investigated allows the realization of a very small distance between the fiber and the surface. Additionally a fiber is very small and flexible, so that the fiber can additionally be positioned at different angles of incidence at the surface.

This allows the use of an external radiation source which is advantageous because a small measuring head can be realized and the radiation beam is directed without losses close to the surface to be investigated by the fiber.

According to a further preferred embodiment of the invention, the fiber comprises a radiation receiving part and a radiation emitting part, wherein the radiation receiving part is connected to a radiation source and the radiation emitting part is arranged in the casing in a close distance to the at least one elongated aperture.

A small shape of the measuring head can be realized in that the radiation emitting part of the fiber can be brought in a close distance to the surface. Further, small areas of the sample can be advantageously illuminated. Additionally, a low intensity radiation beam can be used.

Due to the elongated aperture, the high-intensity of the reflected illumination beam and the lower-intensity of the response beam exiting the surface which has been scattered in the sub-surface area can be distinguished, resulting in a measurement of the near field and the far field distribution of the scattered illumination beam in the sub-surface area.

According to a further embodiment of the invention, the at least one elongated aperture comprises a measuring part through which the illumination beam is propagating onto the surface of the sample and a detection part, through which the response beam is propagating to the detection means.

A spatial separation of the illumination beam and the response beam at the location of the elongated aperture is achievable in a small distance above the surface of the skin. With that a shielding of the illumination beam and the response beam is realized.

According to a further preferred embodiment of the invention, a baffle is arranged inside the measuring head in order to shield the illumination beam from the response beam of the fiber in order to realize the illumination part and the detection part in the elongated aperture.

A baffle is a small, thin plate, which can easily be positioned at the base plate in the elongated aperture. In general a plate made of a metal is used. But any other material, which is dense in the sense of the illumination beam, can be used. It is important according to the invention that the material is not translucent for the illumination beam to guarantee the shielding effect.

According to a further preferred embodiment, the baffle is a substantially vertical baffle, wherein the vertical baffle is extending beyond the base plate towards the surface of the sample.

With that the radiation beam, illuminating the surface is shielded from the opening of the elongated aperture and with that from the entrance of the detection component.

The extension of the baffle through the elongated aperture beyond the base plate results in a division of the measuring head in the illumination part and the detection part.

According to a further preferred embodiment, the vertical baffle indents slightly in the surface of the sample in order to prevent the illumination beam to leak from the illumination part to the detection part. This can be caused by small grooves or pits in the surface of the sample, which is the normal situation in case the sample is a human skin.

Due to the translucency of the skin, the illumination beam would leak into the area at the surface of the skin, where the scattered illumination beam is re-emitted. Because the illumination beam has a very high intensity compared to the intensity of the response beam, comprising the deep scattered illumination beam, this would result in an overexposure of the response beam. Therefore, the overexposure of the response beam is prevented with the baffle extending beyond the base plate.

According to a further preferred embodiment of the invention, the detection component comprises a radiation sensitive component, imaging the response beam with respect to the elongated aperture.

The radiation sensitive component is imaging the scattered illumination beam. Preferably, the component has a high sensitivity for radiation in the wavelength range used. In cases where the visual appearance is a subject of investigation, it should also match the sensitivity of the human eye.

The detection component is in general a detector having a radiation sensitive surface which transduces the radiation incident on the radiation sensitive surface into an electrical signal. Using the electrical signal allows the digital storage of the image on storage media like CDs, DVDs and so on.

In the further preferred embodiment of the invention, the radiation sensitive detector is a camera, in particular a digital camera.

A camera is a standard device which can easily be mounted in the optical measurement device. A digital camera has as output a data file including the information of the image suitable for further processing and storage.

According to a further preferred embodiment, the camera comprises a xenon flash for providing the radiation beam.

A separate xenon flash that is triggered by the camera exposure can also be used and is called external flash in the following.

Because most of the cameras have a Xenon flash, emitting a radiation beam with a wide spectral distribution, the use of the Xenon flash is advantageous. No extra radiation source has to be mounted in the measuring head or the optical measurement device. With that, a cheap realization of the optical measurement device can be performed.

Additionally, the standard xenon flash of camera delivers high radiation beam intensities. The use of the xenon flash of the camera allows an easy and cheap synchronization of the illumination of the surface and the detection of the response beam. Additional to the internal or external xenon flash, other light sources such as tungsten halogen, mercury arc lamps LEDs or lasers can be used as a light source.

According to a further preferred embodiment, the detection device comprises at least one color filter. It may also comprise a spectrophotometer or an imaging spectrometer.

The illumination beam scattered in the sub-surface area of the skin which is escaping through the at least one elongated aperture and viewed or imaged by the camera, shows an intensity decay that is depending on the properties of the skin. This causes a distribution of the response beam that can be photographed through the at least one color filter to measure the near field distribution.

Using the at least one color filter allows to make the illumination beam scattered in different depth in the sub-surface area visible, wherein different scatter depth causes different colors in the detected image. The camera visualizes the distribution of the different colors and stores them on the imaging media, either a film material or as a digital data file. Instead of a color filter a so-called color camera can be used, wherein the color filter in included in the camera.

According to a further preferred embodiment of the invention, the color filter is arrangeable in front of the radiation sensitive component.

The response beam has to pass the at least one color filter before being incident on the radiation sensitive component.

According to a further preferred embodiment, the casing comprises a shape such that the optical measurement device fits into a Parousiameter comprising a hemispherical screen for intercepting the response beam.

The Parousiameter, in particular the Parousiameter equipped with additional apertures, allows to measure the far field radiation distributions at the location of the elongated aperture. The elongated aperture is, as mentioned above, about up to 30 mm away from the illumination spot. With that the composition of scatter centers at the sub-surface area of the sample, particular of the skin, can be detected. With that the optical measurement device can serve as a diagnostic tool for the presence and distribution of scatter centers below the skin. A scatter center of interest is, for example, skin cancer. Further characterization of scatter centers can be obtained by using spectral discrimination in the illumination or detection part.

According to a further preferred embodiment of the invention, an entrance plate of the camera extends substantially parallel to the surface of the sample.

This allows a direct imaging of the illumination beam scattered in the sub-surface area of the skin and escaped through the at least one elongated aperture without losses. This is because the scattered beam, the response beam is directed forward, that means substantially having a perpendicular component to the surface of the sample.

According to a further preferred embodiment, the illumination beam propagates along an optical axis defined by the fiber, wherein the optical axis has an angle of incidence that is adjustable with respect to the surface of the sample.

Due to the fact that the fiber can be mounted at different angles in the casing, the angles of incidence of the illumination beam are variably chosen. Due to the different angles of incidence, different penetration depths for the respective illumination beam are achievable. Herein, the angle of incidence varies between 90° and 0°. An angle of incidence of 0° results preferably in the highest penetration depth into the sub-surface area of the sample. A smaller angle of incidence results in a smaller penetration depth due to the fact that the path of the illumination beam through the sample is longer.

Therefore, a measurement of the optical appearance can include different series of measurements taken with an illumination beam at different angles of incidence and detecting the respective response beam. With that the measurement gives access to different depths beyond the surface of the skin, in particular different sized sub-surface areas.

According to a further preferred embodiment of the invention, the angle of incidence is larger than 10° and smaller than 70°.

These angles of incidence are realized in particular in that the fiber is positioned close to the surface of the sample and arranged in the measuring head in such that the optical axis of the fiber inclines at angles adjustable between 10° and 70°. With that sub-surface areas of interest having different sizes (in particular being in different depths beyond the surface of the skin) can be inspected.

The object is solved by a method for measuring the optical appearance of a translucent surface of a sample, in particular a human skin, according to the method mentioned at the outset, in that a response beam, resulting from the illumination beam scattered below the surface in a sub-surface area, is detected and the illumination beam directly reflected is cut off.

The illumination beam directly reflected from the surface of the sample is of high intensity and the illumination beam scattered in a sub-surface area of the sample is a lower intensity beam, wherein the differences are in an order of 10 to 100.

If both, the reflected and the deep scattered response beams would be detected, the detection device has to cover a large intensity range. This would lead to a low resolution concerning the intensity. If only the small intensity response beam is detected by the detection device, the resolution of the intensity can be increased. With that the measurement is more sensitive for the detection of the scatter centers causing the scattering of the illumination beam.

According to a preferred aspect of the method, the response beam is shielded from the illumination beam.

This is advantageous, because the illumination beam would cause overexposure of the response beam.

The optical measurement device is applicable for investigation of translucent materials, in particular for inspection of the skin of a human being and/or the hair of a human being.

In particular, the optical measurement device according to the invention is able to investigate the sub-surface area of the skin, containing for instance blood perfusion, melanin content, oxygen saturation, glucose levels, other metabolic factors and so on.

If an illumination beam is incident on a translucent surface, depending on the illumination angle and the local optical properties of the surface, a scatter field is formed in a sub-surface area of the skin, with the intensity decreasing outward. The intensity decay in the illumination plane is visible in an elongated aperture of the optical measurement device. This is due to the fact that the exciting illumination beam is strong near the area of illumination and fainter some distance away, and most likely has a different direction distribution.

The distribution of the response beam passing the elongated aperture forms the so-called near field and can be measured with a camera in a sample setup. The camera records an image of the light distribution in the elongated aperture that can be analyzed in the computer for three standard color channels, which is a standard procedure and not explained here. The illumination is performed by the illumination device, which comprises preferably a radiation source and a fiber, directing the illumination beam onto the surface of the skin at different angle of incidence, in order to realize different penetration depths of the illumination beam into the sample.

The foregoing and further and more specific objects and advantages of the present invention will become readily apparent for those skilled in the art following detailed description of preferred embodiments thereof, taken in conjunction with the drawings, in which.

Figure 1:
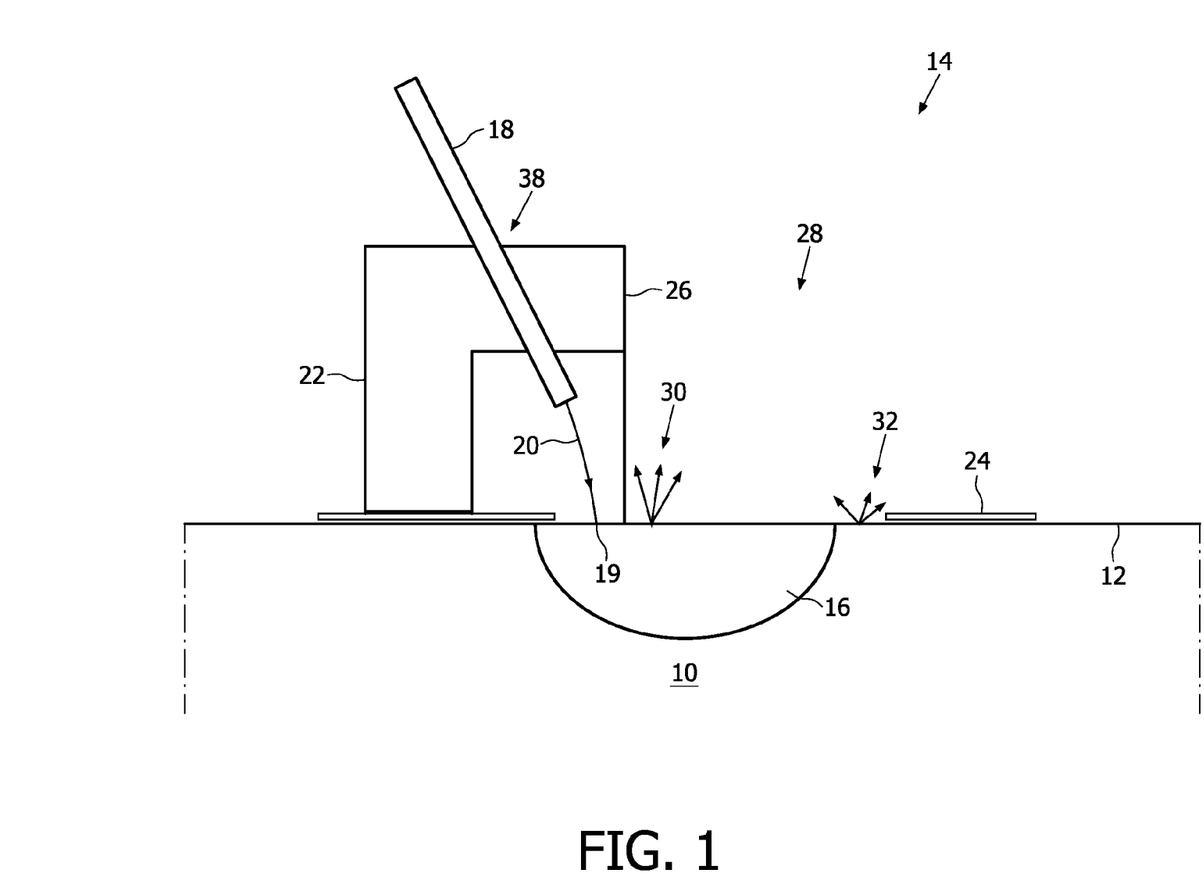
FIG. 1 shows a cross-sectional, schematic view of a measuring head positioned onto a surface of a sample.

In FIG. 1 an optical measurement device 9 is shown, wherein the optical measurement device is positioned onto an object 10, called in the following "sample 10", wherein the object has a surface 12 to be investigated. A measuring head 14 of the optical measurement device 9 is in contact with the surface 12 of the object 10, wherein the sample 10 is in the following a translucent sample.

Translucent objects are in particular a human skin and a human hair. The optical measurement device is explained in the following in accordance with the inspection of the human skin, but can also be applied to the inspection of other translucent samples, like polymere samples, crystalline samples, or turbid liquids like mild or beer contained in a transparent plastic container and the like.

Therefore, the optical measurement device is not limited to the use as a device for the inspection of the human skin. Translucent objects are distinguished by the fact that light incident on the surface 12 is scattered at the surface 12 as well as below the surface 12. That means that the radiation is penetrating into the material of the sample to a certain depth. The light, called illumination beam 20 is therefore scattered at scatter centers of the material and exits the surface 12 at a different location than the location of the incident illumination beam 20. The area, the illumination beam 20 hits the surface 12 and is called illumination spot 19.

The illumination beam 20 is penetrating into the sample 12 and the intensity decays roughly by 1/e length, called intensity decay function. For skin, the illumination beam penetrates about several centimeters in the depth of the skin and is scattered around by various scatter centers present in a sub-surface area of the skin such as bone, cartilage, adipose tissue, connective tissue, collagen, blood and others.

The illumination beam 20, which penetrates in the skin, scatters away, re-emerges several millimeters to centimeters away from the illumination spot 19. Therefore, if the scattered illumination beam 20 has to be detected and measured, this gives an information about the composition of the material in the subsurface area as well as about the concentration of specific scatter centers.

It is necessary to perform the measurement of the scattered illumination beam several centimeters away from the area of the illumination spot 19. The area in which the scattering takes place, resulting in a re-emerged response beam, is expressed as scatter field 16.

The measuring head 14 comprises a fiber 18 directing a first radiation beam 20, called illumination beam 20, onto and/or into the surface 12 of the sample 10.

The measuring head 14 comprises a casing 22. The casing 22 comprises a base plate 24, wherein the base plate 24 is positioned close to the surface 12 of the object 10 during the measurement process. A typical distance of the base plate 24 from the surface of the skin according to the present invention is in the range of micrometers to millimeters, or there can be direct contact.

The measuring head 14 additionally comprises a vertical baffle 26, wherein the baffle 26 separates the illumination beam 20 from the response beam 28 exiting the surface 12 of the sample 10. The response beam exiting away from the illumination spot 19 is labeled with the reference number 32. Herein, the response beam 28 comprises the illumination beam scattered close to the illumination spot 19, labeled with the reference number 30 and the illumination beam scattered in the sub-surface area of the skin labeled with the reference number 32.

The vertical baffle 26 is made of a very thin, not transparent plate, preferably a metal plate, and extends during the measurement beyond an elongated aperture 40 in the base plate 24 towards the surface 12 of the skin. The extension is about 0.3 mm beyond the base plate 24, resulting in a slight indent into the surface 12. With that it is prevented that direct radiation, the illumination beam, leaks from the illumination part 34 into the detection part 36.

The measuring head 14 is realized such that different angles of incidence for the illumination beam 20 can be realized. The fiber 18 is therefore mountable in different bores 38 of the casing 22, wherein only one bore 38 is shown in FIG. 1.

The unused bores are closed with plugs 39 in order to prevent radiation emitting from the measuring head 14. Depending on the angle of incidence of the illumination beam and the local optical properties of the skin, the scatter field 16 is formed in the sample 10, in particular in the skin to be investigated, wherein the intensity of the illumination beam 20 decreases outward. The intensity decay of the illumination beam 20 in the illumination plane is visible in the elongated aperture 40. The elongated aperture 40 is arranged in the base plate 24 and has a length 42 which extends more than a factor of approximately five over the width of the elongated aperture 40 in the base plate 24. The light distribution, comprising the illumination beam scattered at the surface of deep scattered in the sub-surface area is detected in general with a detection device 56, not shown in FIG. 1 comprises a radiation sensitive component 56a, which is a camera 56b, forming a two-dimensional image out of the intensity pattern.

The image comprises an intensity distribution due to the different intensity of the illumination beam 20 near the illumination spot 19 and the intensity of the response beam 28, which is emerged from the sub-surface area in a distance away from the illumination spot 19.

Therefore, the elongated aperture 40 is important in order to gain the response beam 28 comprising the spatial distribution with respect to the surface. The optical measuring device 9 can be modified such that both the illumination beam 20 scattered in a first depth of the sample and the scattered in greater depths below the surface can be detected in general and spatially resolved detected.

The skin to be investigated, is varying widely between individual people and is also varying widely between various body parts. The composition and the concentration of scatter centers can be determined out of the measured image comprising an intensity distribution of the scattered beams 30 and the intensity of the deep scattered beam 32. Also the investigation of the translucence of hairs, in particular a strand of hairs, is possible, while the translucency results in an azimuthal scatter bow.

Figure 2:
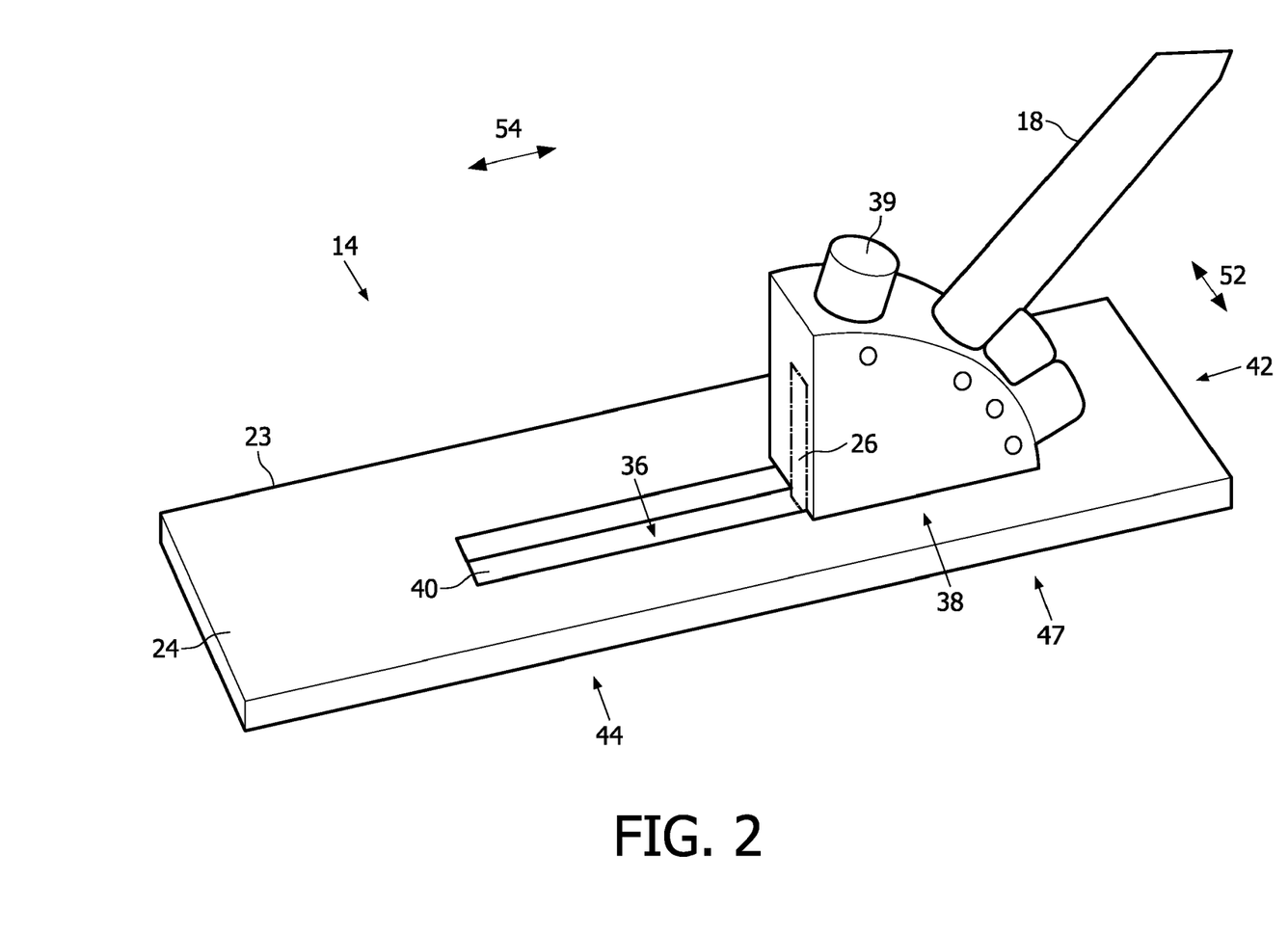
FIG. 2 shows a schematic view of one embodiment of the measuring head.

FIG. 2 shows the optical measurement device in a perspective view. The same parts are assigned with the same reference numerals as in FIG. 1.

The base plate 24 comprises a rectangular shape with a longer side 42 and a smaller side length 44. The bottom of the base plate 24 is in contact with the surface 12 of the sample 10. The top side 46 of the base plate 24 is connected to the casing 22 including the fiber 18. The elongated aperture 40 is reaching from the top side 46 to the bottom side 47 and has a rectangular shape or other shape, such as a pie section.

The fiber 18 is directed to the measuring part 24 of the elongated aperture 40 in order to illuminate the surface 12. The scattered illumination beams 30, 32 propagate through the elongated aperture 40, wherein the light reflected at the surface is cut off, because it is reflected at the illumination spot 19 covered with the casing 22. It can be seen that the optical measurement device 9 can be moved along the surface 12 of the sample 10 inspecting the surface 12 and sub-surface area. The movement can be in two directions indicated with the arrow 52 and the arrow 54. At each measuring position an image of the response beam 28, which has propagated through the elongated aperture 40 is taken by a camera 56b, not shown in FIG. 2.

The vertical baffle 26 is indicated with a rectangular area in dotted lines. The vertical baffle 26 can be mounted inside the casing 22 where the fiber 18 is mounted in or at a side plate as indicated in FIG. 2.

Figure 3:
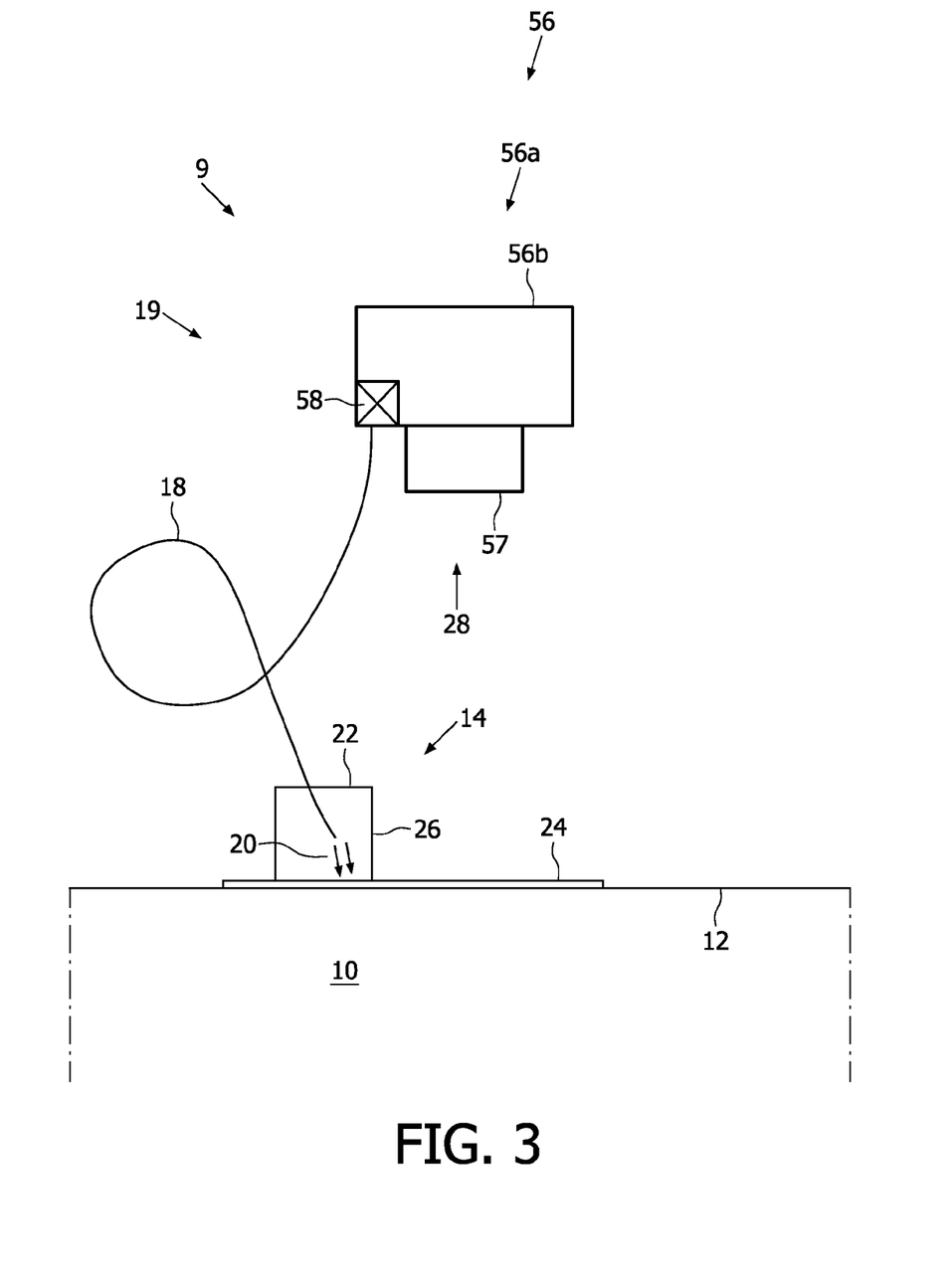
FIG. 3 shows a cross-sectional, schematic view of an illumination device and a detection device.

FIG. 3 shows the optical measuring device 14 positioned in a measuring position on the surface 12 of the sample 10 to be investigated. The base plate 24 is positioned nearly parallel to the surface 12. The casing 22 includes the fiber 18, in order to illuminate the surface 12. A camera 56 is positioned such that an image of the response beam 28 is propagated through the elongated aperture 40, not visible here, can be taken. The radiation beam which is directed through the fiber 18 in order to form an illumination beam at the surface 12 originates from a radiation source 58 which is preferably the xenon flash of the camera 56. This has the advantage that the illumination of the surface 12 can easily be synchronized by the starting of the camera 56 taking the image of the response beam 28.

Figure 4:
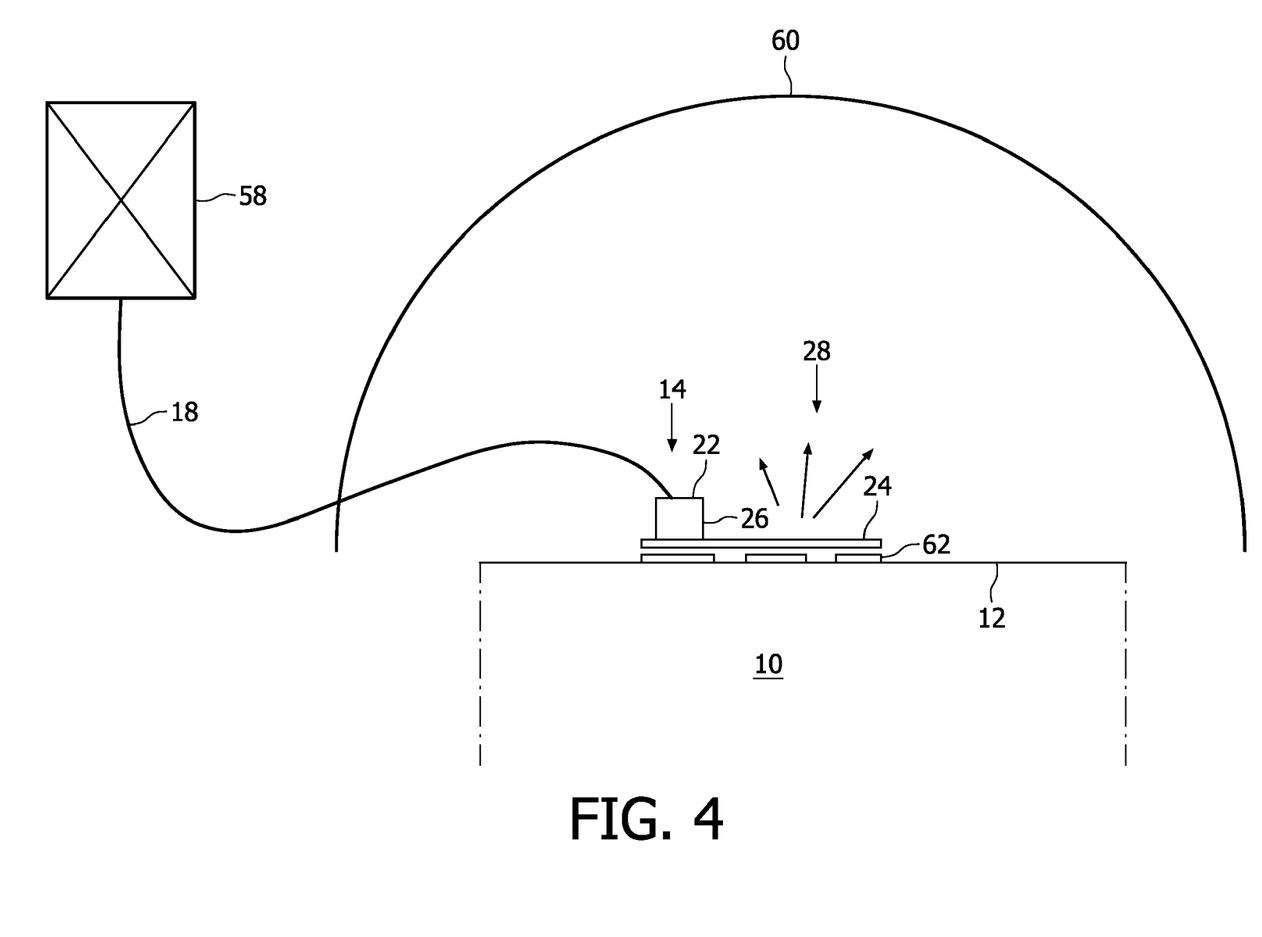
FIG. 4 shows a schematic view of a measuring head implemented in a Parousiameter.

FIG. 4 shows a further embodiment of the invention, wherein the optical measuring device 14 is included in a standard Parousiameter, having a hemispherical screen 60. Herein, the surface 12 is illuminated by the illumination beam 20, which is directed by the fiber 18 onto the surface 12. The base plate comprises a masked aperture 62.

A measurement can be performed taking an image of the near field with the camera 56b at the far field using the hemispherical screen 60. The two-dimensioned picture intercepted by the screen 60 is taken by the camera 56b in order to store the information and obtain a correlation factor between a scattering distribution and features of the optical appearance.

Figure 5:
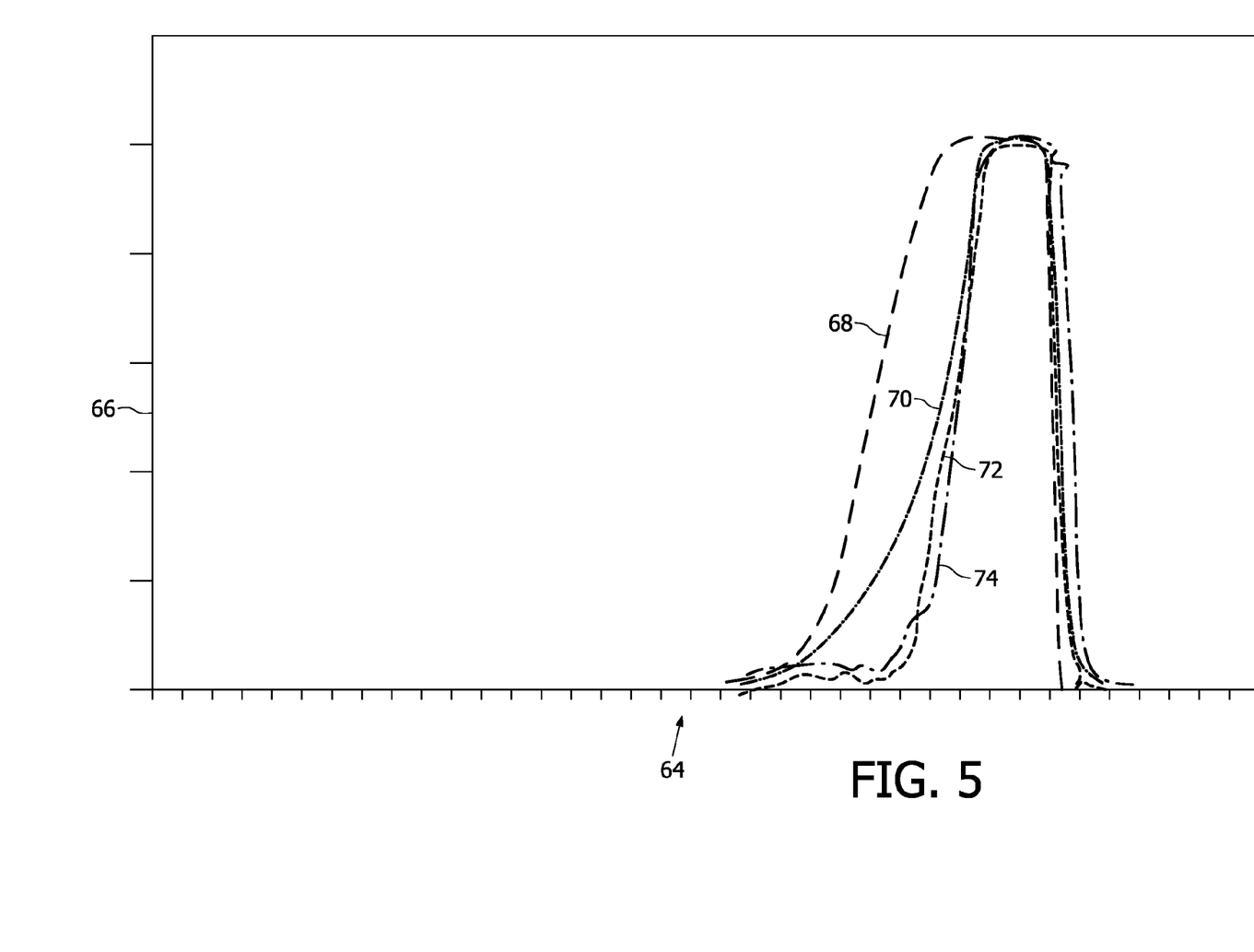
FIG. 5 shows a diagram of a near field information taken from the response beam.

FIG. 5 shows an analysis of the near field scatter intensity decay. The x-axis 64 indicates the distance from the illumination spot 19 and the y-axis 66 shows the intensity. Curve 68 shows the overall integrated intensity, emitted through the elongated aperture. Curve 70 shows the intensity for the scattered illumination beam that is emitted at a wavelength of the red color, curve 72 shows the emitted intensity for the green color and curve 74 shows the emitted intensity for the blue color.

From these intensity curves, the number and nature of scatter centers responsible for the scattering of the illumination beam 20 can be processed.

The intensity measurement has been performed using a camera. the camera 56b records an image of the distribution of the response beam in the elongated aperture and the intensity curves have been analyzed using a computer program for the three standard color channels.

The invention claimed is:

1. An optical measurement device for measuring an optical appearance of a surface of a sample of a human skin, wherein the surface is at least partly translucent, the optical measurement device comprising:
   an illumination device for illuminating the surface with an illumination beam wherein the illumination beam is generated from a radiation beam emitted from a radiation source;
   a detection device for intercepting a response beam generated as a response of the sample to the illumination beam, incident on the surface;
   a measuring head comprising a base plate that can be brought into contact with the surface of the sample, wherein the base plate comprises at least one elongated aperture, which is designed such that the response beam, generated below the surface in a sub-surface area of the sample, is detectable by the detection device, wherein the base plate is arrangable at the surface of the sample in order to perform a measurement of the optical appearance and the illumination beam directly reflected at the surface is cut off.

2. The optical measurement device of claim 1, wherein the measurement head comprises a casing.

3. The optical measurement device of claim 1, wherein the illumination device comprises a fiber, wherein the radiation beam is directed by means of the fiber as the illumination beam illuminates the surface of the sample.

4. The optical measurement device of claim 3, wherein the fiber comprises a radiation receiving part and a radiation emitting part, wherein the radiation receiving part is connected to the radiation source and the radiation emitting part is arranged in the casing a close distance to the least one elongated aperture.

5. The optical measurement device of claim 1, wherein the at least one elongated aperture comprises an illumination part through which the illumination beam is propagating onto the surface and a detection part, through which the response beam is propagating towards the detection device.

6. The optical measurement device of claim 1, comprising a baffle arranged inside the measuring head to shield the illumination beam from the response beam.

7. The optical measurement device of claim 6, wherein the baffle is a substantially vertical baffle extending beyond the base plate towards the surface of the sample.

8. The optical measurement device of claim 7, wherein the vertical baffle indents slightly in the surface of the sample in order to prevent the illumination beam leaking from the illumination part to the detection part.

9. The optical measurement device of claim 1, wherein the detection device comprises a radiation sensitive element, imaging the response beam with respect to the elongated aperture.

10. The optical measurement device of claim 9, wherein the radiation sensitive element is a camera.

11. The optical measurement device of claim 10, wherein the camera comprises a xenon flash for providing the radiation beam.

12. The optical measurement device of claim 9, wherein the detection device comprises at least one color filter.

13. The optical measurement device of claim 12, wherein the at least one color filter is arrangeable in front of the radiation sensitive element.

14. The optical measurement device of claim 2, wherein the casing comprises a shape such that the optical measurement device fits into a Parousiameter, comprising a hemispherical screen for intercepting the response.

15. The optical measurement device of claim 10, wherein the camera comprise an entrance plane that extends substantially parallel to the surface of the sample.

16. The optical measurement device of claim 3, wherein the illumination beam propagates along an optical axis defined by the fiber that has an angle of incidence that is adjustable with respect to the surface of the sample.

17. The optical measurement device of claim 16, wherein the angle of incidence is adjustable between 10° and 70°.

18. The optical measurement device of claim 14, wherein the optical measurement device is suitable of obtaining a Parousiagram for measuring a near field, wherein the near field is the illumination beam scattered at the surface and measuring a far field, wherein the far field is the illumination beam scattered below the surface.

19. A method for measuring an optical appearance of a translucent surface of a sample of a human skin, the method comprising acts of:
   illuminating the surface of the sample with an illumination beam;
   providing a measuring head comprising a base plate with at least one elongated aperture;
   detecting with the measuring head a response beam generated as a response of the sample to the illumination beam incident on the surface while the base plate is arranged at the surface of the sample;
   wherein the at least one elongated aperture is provided such that the response beam resulting from the illumination beam scattered below the surface in a sub-surface area is detected, and the direct reflected illumination beam is cut off.

20. The method of claim 19, comprising an act of detecting additionally the response beam generated from the illumination beam scattered at the surface.

21. The method of claim 20, comprising an act of shielding the response beam from the illumination beam.

* * * * *